United States Patent [19]

Cialkowski et al.

[11] Patent Number: 5,387,322
[45] Date of Patent: Feb. 7, 1995

[54] FUSEL OIL STRIPPING

[75] Inventors: Edward J. Cialkowski, Houston; Girish C. Joshi, Sugar Land; Robert V. Schneider, III, The Woodlands, all of Tex.

[73] Assignee: The M. W. Kellogg Company, Houston, Tex.

[21] Appl. No.: 61,870

[22] Filed: May 14, 1993

[51] Int. Cl.[6] .............................................. B01D 3/26
[52] U.S. Cl. ................................... 252/158; 202/234; 203/96; 203/DIG. 9
[58] Field of Search ................. 202/234, 158; 203/96, 203/DIG. 9; 196/127; 210/180; 518/704

[56] References Cited

U.S. PATENT DOCUMENTS

| | | | |
|---|---|---|---|
| 2,113,130 | 4/1938 | Dunham | 203/96 |
| 3,503,854 | 3/1970 | Good | 202/234 |
| 3,544,428 | 12/1970 | Mellbom | 203/96 |
| 3,682,779 | 8/1972 | Ritter et al. | 203/96 |
| 4,001,347 | 1/1977 | Grosick | 203/96 |
| 4,342,735 | 8/1982 | Tsao | 203/96 |
| 5,167,773 | 12/1992 | Eagan | 203/DIG. 9 |

Primary Examiner—Christopher Upton
Attorney, Agent, or Firm—John P. Ward

[57] ABSTRACT

A method for recovering volatile components from reformer effluent condensate and fusel oil in a methanol plant is disclosed. The fusel oil is stripped with steam to produce an overhead vapor stream of steam and stripped organic components which is recycled to the feed to the reformer. Also disclosed are a methanol plant with a fusel oil stripper; and a unitized stripper column for treating fusel oil and process condensate wherein steam containing volatile gases stripped from the process condensate is used to strip the fusel oil. The present invention improves yield and reduces or eliminates liquid fusel oil waste by recycling volatile organic components contained in the fusel oil to the feed of the reformer.

1 Claim, 2 Drawing Sheets

FUSEL OIL STRIPPING

FIELD OF THE INVENTION

The present invention relates to a methanol plant, and in particular to substantially reducing or eliminating the amount of fuel oil waste incinerated or otherwise disposed of.

BACKGROUND OF THE INVENTION

Efforts to reduce manufacturing costs of chemical products are on-going. Particular attention has been directed to reducing energy costs by implementing heat integration design, that is, the process-wide pairing of heat-releasing streams with heat-accepting streams. In addition, energy usage has been lowered by the adoption of more thermodynamically efficient design of unit processes such as distillation, heat exchange, and the like. It is also advantageous to reduce the production of liquid waste streams to lessen incineration or other disposal costs which are imposed by ever-increasing environmental concerns.

In methanol production, fusel oil comprising primarily aqueous methanol and other volatile organic reaction by-products is a primary liquid waste stream. It has been known to recycle the crude, untreated fusel oil stream to the reformer feed, either directly to the reformer inlet coils or by means of a feed gas saturator on the reformer hydrocarbon gas feed. This has the potential for damaging the reforming catalyst if the fusel oil contains any solids such as methanol synthesis catalyst particles, caustic or other components carried over from the methanol synthesis that can damage the reforming catalyst. More commonly, fusel oil waste streams have been burned as fuel to heat a reformer. However, recent environmental thinking regards fusel oil as a hazardous material unsuitable for incineration, and has potentially increased the cost and complexity of fusel oil disposal. Thus, it would be beneficial to recover the methanol and other reaction by-products from these fusel oil waste streams to concurrently enhance product yield and eliminate these liquid waste streams, and thus address these environmental concerns.

SUMMARY OF THE INVENTION

This invention is directed to a method and apparatus for stripping fusel oil produced in a methanol plant to permit the recovery and recycle of a major proportion or all of the volatile organic components in the fusel oil to the reformer, and to minimize the proportion of the volatile organic components disposed of as a waste stream. In such a manner, the yields of synthesis gas, and consequently methanol, are enhanced and the volume of potentially hazardous liquid waste produced is reduced.

Broadly, the present invention provides a methanol plant in which a major proportion or all of the volatile organic components of the fusel oil can be efficiently recovered and recycled as feed to a synthesis gas reformer. The methanol plant has the generally conventional reforming unit for reacting steam and hydrocarbon gas feed to produce a synthesis gas; a heat recovery zone for cooling and recovering heat from the synthesis gas; a condensate separation zone for recovering process condensate from the synthesis gas; a syngas compression zone for compressing the synthesis gas; a methanol synthesis zone for synthesizing methanol from the compressed synthesis gas; and a distillation zone for refining the synthesized methanol while also producing a waste fusel oil stream. The present methanol plant further includes a fusel oil stripper for stripping volatile organic components from the fusel oil, and has a recycle line for feeding the stripped organic components to the hydrocarbon gas feed to the reforming unit.

In one embodiment, the present invention provides a method for recovering volatile gases from reformer effluent condensate and volatile organic components from methanol synthesis byproducts. As one step, process condensate, containing minor amounts of primarily inorganic components mostly in the form of dissolved and/or condensed gases, is separated from the reformer effluent. As another step, the methanol synthesis effluent is distilled into a high purity methanol fraction, a fusel oil fraction, and a bottoms fraction. The process condensate is fed to a first stripping zone and the fusel oil fraction is fed to a second stripping zone. The process condensate is stripped of the volatile gases with steam in the first stripping zone to produce an enriched overhead vapor stream and a stripped process condensate bottoms stream. The fusel oil is stripped in the second stripping zone, preferably with the overhead vapor stream from the first stripping zone, to produce an organics-rich overhead vapor stream and a second stripped bottoms stream. The overhead stream from the second stripping zone is recycled to the reformer feed. The first stripping zone is preferably disposed below the second stripping zone in a unitized stripping column including a liquid collector, disposed between the first and second stripping zones, which receives liquid from the second zone as a second stripped bottoms stream and which further allows vapor to pass from the first zone to the second zone.

In a preferred embodiment, the present invention provides a unitized stripper for fusel oil and process condensate in a methanol plant. The stripper comprises a lower stripping zone including a process condensate inlet, a stripping steam inlet, and vapor/liquid contact elements disposed between the inlets. A first liquid outlet is disposed, generally at a lower end of the lower stripping zone, for removing stripped condensate therefrom. The stripper further comprises an upper stripping zone including a fusel oil inlet, a liquid collector for receiving the second stripped bottoms stream from the upper stripping zone and vapor/liquid contact elements disposed between the fusel oil inlet and the liquid collector. The stripper preferably has a second liquid outlet in fluid communication with the liquid collector for removing liquid therefrom; a passage, preferably disposed in the liquid collector, for vapor to pass from the lower stripping zone into the upper stripping zone; and a vapor outlet, preferably adjacent to a top of the upper stripping zone, to recover the an organics-rich vapor overhead stream containing organic components and volatile gases stripped from the fusel oil and the process condensate, respectively. A recycle line is provided to recycle the recovered organics-rich vapor overhead stream to an inlet of a reforming reactor.

In addition to the environmental and economic advantages associated with the recycle of the volatile organic components recovered from the fusel oil recycle discussed above, the unitized stripper for the fusel oil and process condensate has the further advantages of conserving energy requirements for operation of the unitized stripper as well as reduced equipment costs of the unitized stripper, compared to separate fusel oil and process condensate stripping units.

The present concept of purifying aqueous streams such as the process condensate and fusel oil, is also applicable to the processing of other aqueous waste streams in conjunction with the operation of a reformer for the production of synthesis gas, either for ammonia or methanol manufacture. In a much broader sense, then, the present invention provides a method for purifying aqueous waste streams in conjunction with the operation of a synthesis gas unit. The method includes the steps of feeding steam and hydrocarbon to a reforming zone; feeding an aqueous waste stream comprising volatile organic components to a steam stripper; recovering an organics-lean, purified condensate stream from the stripper; recovering an organics-rich vapor stream from the stripper; and introducing the organics-rich vapor stream into feed to a reforming zone. This aqueous waste stream methodology can also be combined with the recovery and stripping of process condensate. Thus, the method can also include recovering effluent from the reforming zone; cooling the recovered effluent to form process condensate; separating the process condensate from the cooled effluent; and feeding the process condensate separated from the effluent to a first stripping zone in the steam stripper to strip dissolved gases from the process condensate, obtain an overhead vapor stream enriched in the dissolved gases, and a purified process condensate stream. The overhead vapor stream from the first stripping zone is preferably fed to a second stripping zone, wherein the vapor stream from the first stripping zone is used as a steam supply to strip the aqueous waste stream in the second stripping zone. The organics-rich vapor stream recovered from the stripper and introduced to the feed to the reforming zone contains the volatile gases stripped from the process condensate. This methodology is applicable to various aqueous waste streams, such as, for example, bottoms from a methanol refining column, fusel oil, bottoms water from a scrubber such as in an atmospheric vent, steam condensate imported from another process unit, etc.

DETAILED DESCRIPTION OF THE INVENTION

Figure 1:
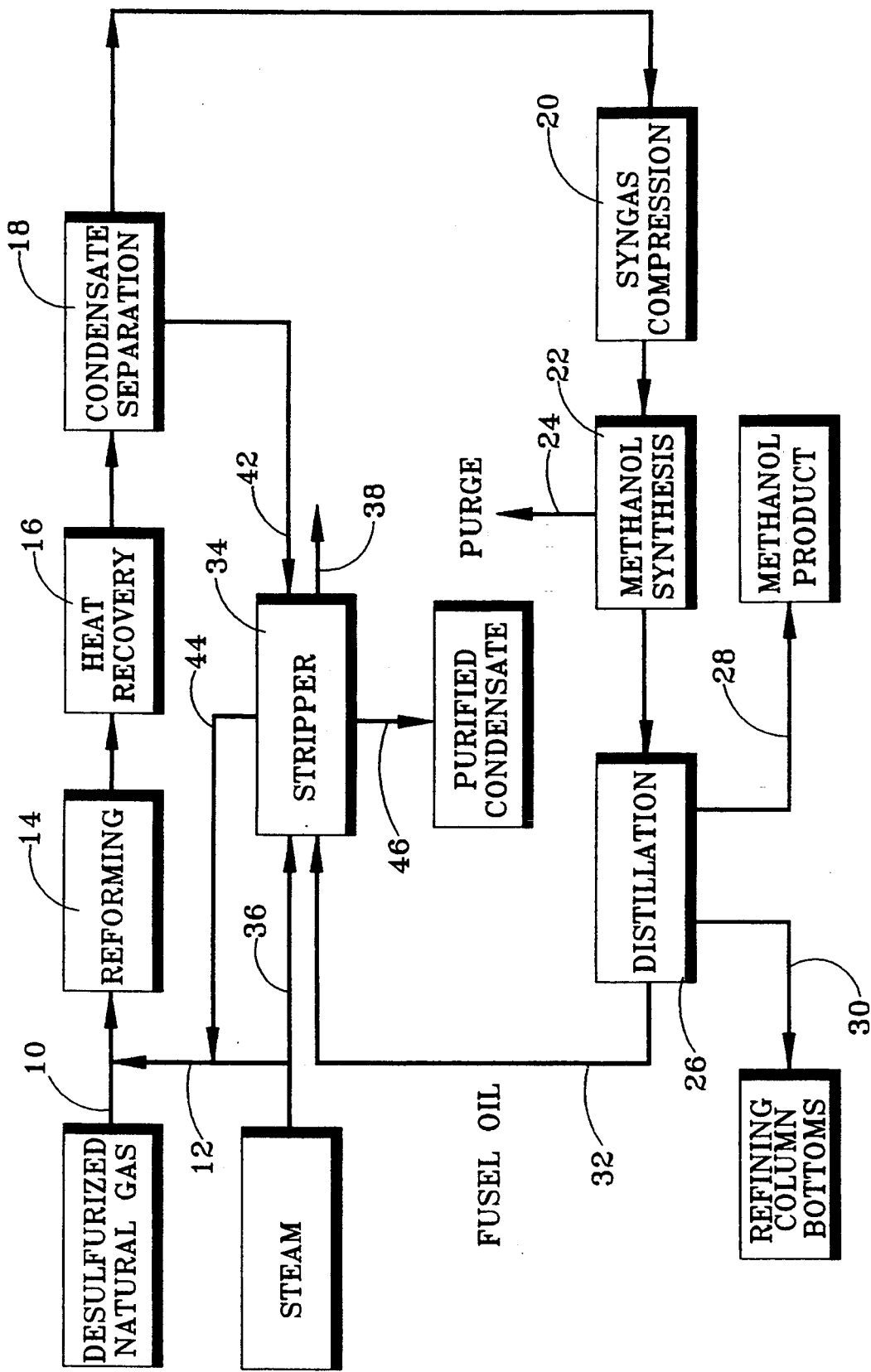
FIG. 1 is a block diagram of one embodiment of the methanol process of the present invention showing a combined fusel oil/process condensate stripping zone.

Improvements to a catalytic methanol process include the use of a preferably unitized process condensate/fusel oil stripping column to strip and recover volatile organic components contained in the waste fusel oil. An overview of the methanol process according to a preferred embodiment of the present invention is shown in terms of the major plant streams in FIG. 1. A gaseous, desulfurized hydrocarbon feed under pressure at a temperature on the order of 370° C. (700° F.) is typically introduced through line 10. The hydrocarbon feed is typically methane or natural gas, but other hydrocarbon feeds can be used.

The desulfurized hydrocarbon gas is conventionally mixed with steam from line 12 and heated to an inlet temperature of a reforming zone 14 on the order of 620° C. (1150° F.). A molar ratio of steam to atomic carbon of the feed gas is generally about 3 to 1. As is known in the art, much of the hydrocarbon feed is decomposed in the reforming zone 14 to $H_2$, CO and $CO_2$ to produce a methanol synthesis gas. The reforming zone 14 is typically operated at a pressure on the order of 1.7–2.4 MPa(g) (250–350 psig) and at a temperature of from about 790° C. to about 900° C. (1450° F.–1650° F.). The reforming zone 14 contains a conventional catalyst, e.g. nickel on alumina, and is heated conventionally, e.g. in the radiant heating chamber in a fired furnace.

The methanol synthesis gas from the reforming zone 4 is directed to waste heat recovery equipment 16 wherein sensible and condensing heat of the gas is used to perform a variety of heating duties such as, for example, heating boiler feed water, vaporizing crude methanol, and the like. Heat transfer against process and utility streams in a manner well known in the art preferably cools the synthesis gas to a temperature of about 35° C. to about 40° C. (95°–104° F.).

Since the synthesis gas from the reformer contains excess steam, this steam becomes condensed and is removed in a process condensate separation stage 18. The separation stage 18 is made up of a separation vessel or other conventional equipment. The process condensate recovered in the condensate separation stage 18 generally contains a minor proportion of primarily inorganic components, mostly in the form of condensed or dissolved gases, such as ammonia, methane, carbon monoxide, carbon dioxide, nitrogen, and the like. For the purposes of clarity and simplicity, these components are collectively referred to herein as volatile gases. Of these volatile gases, ammonia at a typical concentration of about 100–400 ppm is the most difficult to strip and can require 3 or 4 theoretical stages to reduce to an acceptable concentration, e.g. 5 ppm. The process condensate is usually fed in line 42 to stripper stage 34 where it is steam stripped with steam from line 36 to obtain a purified condensate stream 46, which can be suitably employed, for example, as boiler feed water for plant steam requirements. The volatile gases stripped from the process condensate are fed via line 44, usually with steam in line 12, to the reforming feed line The cooled methanol synthesis gas is compressed in a conventional compression stage 20 to a suitable methanol synthesis pressure, typically from about 6.2 to about 10.3 MPa(g) (900–1500 psig). The compressed methanol synthesis gas is conventionally introduced to a methanol synthesis unit 22, wherein methanol is produced in the presence of a conventional copper catalyst, for example, at a temperature of from about 210° C. to about 270° C. (410° F.–520° F.).

As is well known in the art, conversion to methanol is incomplete. An effluent from the methanol synthesis unit 22, containing crude methanol, higher molecular weight byproducts and unreacted methanol synthesis gas, is conventionally cooled to condense the methanol formed and uncondensed methanol synthesis gas is recycled. A portion of the unreacted synthesis gas is withdrawn as a purge gas stream in line 24 in order to avoid accumulation of methane, nitrogen, and other inert substances, as well as excess hydrogen. The hydrogen in the purge gas can be used as a raw material in other synthesis reactions, e.g., ammonia synthesis or as a fuel.

The crude methanol is directed to a methanol purification zone 26 wherein impurities formed during the methanol synthesis are generally removed by distillation. A refined methanol stream is recovered through line 28. A distillation bottoms waste stream comprising primarily water and trace amounts of methanol, higher alcohols and paraffinic hydrocarbons is withdrawn through line 30. Some impurities formed as a by-product of the catalytic methanol reaction are typically removed as a fusel oil fraction through line Heretofore, fusel oil, comprising an aqueous mixture of volatile organic components including primarily methanol (approximately 30–40 percent by weight) with a small amount of ethanol and other heavier components, has usually been burned along with other fuels to heat the reforming furnace. However, to reduce the production of a potentially hazardous waste material and lessen the disposal costs and environmental impact of methanol production, it has been found that these volatile organic compounds contained in the fusel oil fraction can be advantageously stripped from the fusel oil and recycled to the reformer feed.

In the present process, the fusel oil in line 32 is preferably stripped in a fusel oil stripping zone 34 to obtain an organics-rich vapor stream which can be recycled to the reforming feed stream 10. The fusel oil stripping zone 34 preferably comprises a fusel oil stripping column wherein steam introduced in a line 36 is used to strip the organic components from the aqueous fusel oil to obtain the organics-rich vapor stream, and an organics-lean liquid stream. The organics-lean liquid stream is removed from the stripping zone 34 through line 38 for further treatment, if desired, and disposal. The organics-lean stream in line 38 comprises water containing, for example, from about 20 to about 100 ppm by weight of methanol and from about 0.1 to about 5 ppm by weight ethanol.

To reduce capital outlays, the fusel oil stripping column is preferably unitized with a process condensate stripping column (see FIG. 2 discussed below). As previously mentioned, the stripping zone 34 also has a process condensate feed through line 42 and steam is used to substantially strip the dissolved gases from the process condensate. The organics-rich vapor stream thus obtained from the fusel oil and condensate feeds is removed in line 44. The organics-rich stream is recycled to the hydrocarbon feed line 10 at the front of the methanol process. The organic components thus recycled, are generally decomposed with the bulk of the hydrocarbon feed, as mentioned above, into hydrogen, carbon monoxide and carbon dioxide comprising the methanol synthesis gas. The hydrocarbon feed in line 10 and/or the steam feed in line 12 can be adjusted to maintain a desired feed rate and carbon:steam molar ratio. The purified process condensate stripped of volatile gases is removed from the stripping zone 34 in line 46. The purified process condensate can be used in boilers, for example, as is well known in the art.

Figure 2:
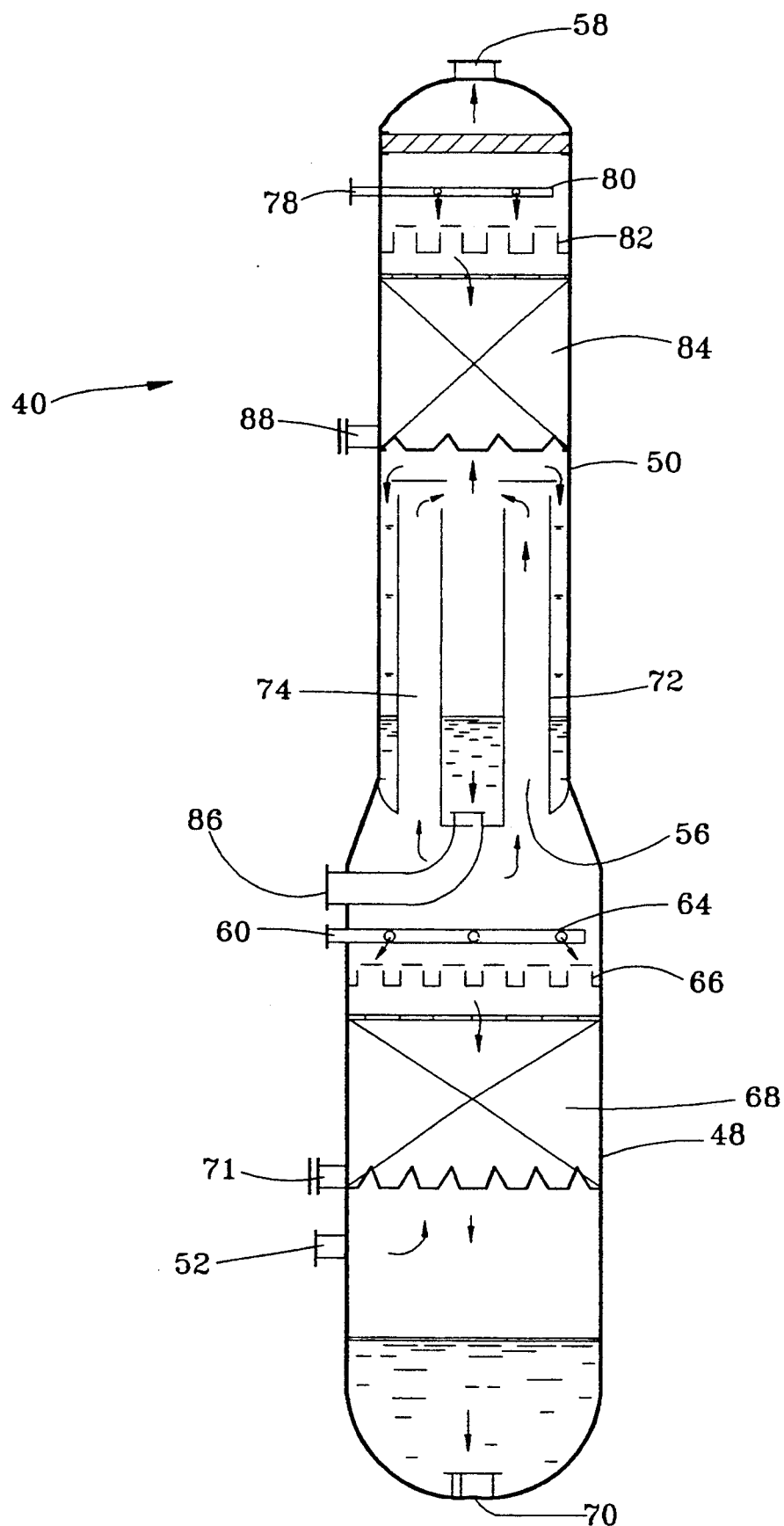
FIG. 2 is a schematic process diagram of a combined fusel oil/process condensate stripper of the present invention.

With reference to FIG. 2, an exemplary design of the present unitized process condensate/fusel oil stripper 40 has a lower process condensate stripping zone 48 and an upper fusel oil stripping zone 50. Stripping steam is introduced at a lower end of the lower condensate stripping zone 48 through port 52. Steam and stripped vapors pass upwardly through the lower stripping zone 48 to an inlet 56 at a lower end of the upper stripping zone 50 for stripping fusel oil in the upper stripping zone 50. Steam, containing organic components stripped from the fusel oil and dissolved gases stripped from the process condensate, is removed from the upper stripping zone 50 through outlet 58 adjacent the top.

In the operation of the unitized stripping column 40, the use of countercurrent flow and beds of vapor/liquid contacting packing elements are preferred. Process condensate is fed to an upper end of the lower stripping zone 48 through an inlet 60. A spray nozzle 64 and liquid distribution tray 66 are shown for distributing the process condensate over packing elements disposed in a lower bed 68, although other distributing apparatus can be selected. A purified process condensate is removed from the lower end of the lower condensate stripping zone 48 through an outlet 70. The lower condensate stripping zone 48 preferably has sufficient volume to maintain a suitable liquid holdup level in the lower end. However, the maximum liquid level should be below the level of the steam inlet port 52. The lower bed 68 has a conventional manway 71 for loading and unloading the packing elements.

A liquid collector 72 is preferably disposed between the lower and upper stripping zones 48,50 for receiving liquid from the upper stripping zone 50. The liquid collector 72 has passages 74 to permit steam and stripped gases to pass from the lower stripping zone 48, through the liquid collector 72, into the upper stripping zone 50 for stripping the fusel oil. Fusel oil is fed to the upper end of the upper stripping zone 50 through an inlet 78. A spray nozzle 80 and liquid distribution tray 82 are shown for distributing the fusel oil over packing elements in an upper bed 84, although other suitable distributing apparatus can be selected. A liquid stream substantially stripped of organic components is removed from the upper stripping zone 50 through an outlet port 86 in the liquid collector 72. The liquid collector 72 preferably has sufficient volume to maintain a suitable liquid holdup level. However, the maximum liquid level should be below the top of passages 74. The upper bed 84 also has a conventional port or manway 88 for loading and unloading the packing elements.

The use of beds of vapor/liquid contacting packing elements is preferred to trays to minimize pressure differential and maximize vapor/liquid contact in the unitized column 40. The lower and upper beds 68,84 typically comprise packing rings of suitable size. Other design factors, including design pressure and temperature, length and width of the upper and lower stripping zones 48,50, length of the packed beds 68,84, and the like will depend on ordinary design parameters including operating pressure of the reforming zone flowrate and composition of the fusel oil and process condensate feeds, desired composition of the outlet streams, and the like. In general, adequate stripping is obtained using 3 or 4 theoretical stages in the lower bed 68 and 4 or 5 theoretical stages in the upper bed 84, with from about 0.2 to about 0.4 kg steam per kg of process condensate. The stripper 40 will generally operate at the pressure of the reforming zone 14 to avoid or minimize compression of the organics-rich recycle stream in line 44. Stainless steel or stainless steel clad carbon steel are preferred materials of construction for stripper 40 to minimize corrosion.

A unitized stripper 40 is particularly preferred for treating the fusel oil and process condensate, however, separate columns (not shown) can also be used. In the case of separate columns, steam and process condensate are countercurrently contacted in a first stripping column. An overhead stream therefrom can be directed to a second stripping column and countercurrently contacted with a fusel oil stream. Organics and steam taken overhead from the second stripping column are recycled to the hydrocarbon feed in line 10.

In the practice of the present invention, methanol is produced by the catalytic reaction of a synthesis gas produced by the steam reforming of a hydrocarbon. The crude methanol produced is distilled into a refined product. Liquid waste streams formed, namely process condensate from the reforming stage and fusel oil from the distilling stage are concurrently treated in a unitized steam stripping column to produce an organics-rich stream which is recycled to the reforming zone without adversely impacting the reforming catalyst, although it may be desirable, depending on the catalyst sensitivity to higher alcohols in the feed, to employ a small top layer of slightly alkalized catalyst to prevent any coking by the alcohols. In addition, the purified process condensate and the organics-lean condensate from the fusel oil thus treated can be reused and/or disposed of with facilitated biotreatment and/or fewer adverse environmental consequences due to a reduced quantity and concentration of organic compounds.

The present fusel oil processing method and unitized stripper apparatus are illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

We claim:

1. A unitized stripping column for stripping both fusel oil and process condensate produced in a methanol plant, said stripping column comprising:

a lower stripping section within the stripping column for removing volatile components from the process condensate, the lower stripping section including an upper process condensate inlet, a lower stripping steam inlet, vapor/liquid contact elements disposed between the inlets, and a process condensate distribution means disposed between the process condensate inlet and the vapor/liquid contact elements for distributing the process condensate over the vapor/liquid contact elements;

an outlet disposed at a lower end of the lower stripping section for removing steam stripped process condensate therefrom;

an upper stripping section within the stripping column for removing volatile components from the fusel oil, the upper stripping section including an upper fusel oil inlet, a lower liquid collector for receiving liquid from the upper stripping section, vapor/liquid contact elements disposed between the fusel oil inlet and the liquid collector, and a fusel oil distribution means disposed between the fusel oil inlet and the vapor/liquid contact elements;

a liquid outlet in fluid communication with the liquid collector for removing liquid therefrom;

a passage through the liquid collector for vapor to pass from the lower stripping section to the upper stripping section to strip fusel in the upper stripping section;

a vapor outlet adjacent a top of the upper stripping section to recover a vapor stream comprising steam and volatile components stripped from both the process condensate and fusel oil; and a conduit in fluid communication with the vapor outlet for recycling the recovered vapor stream from the upper stripping section of the stripping column to an inlet of a reforming reactor.

* * * * *